US012697312B2

(12) United States Patent (10) Patent No.: US 12,697,312 B2
Collins (45) Date of Patent: Aug. 4, 2026

(54) METHODS AND DEVICES FOR TREATMENT OF EYELID PTOSIS

(71) Applicant: Atif B. D. Collins, Fresno, CA (US)

(72) Inventor: Atif B. D. Collins, Fresno, CA (US)

( * ) Notice: Subject to any disclaimer, the term of this patent is extended or adjusted under 35 U.S.C. 154(b) by 0 days.

(21) Appl. No.: 18/479,520

(22) Filed: Oct. 2, 2023

(65) Prior Publication Data

US 2024/0173271 A1     May 30, 2024

Related U.S. Application Data

(62) Division of application No. 18/059,350, filed on Nov. 28, 2022, now Pat. No. 11,779,553.

(51) Int. Cl.
*A61K 31/137* (2006.01)
*A61K 31/4174* (2006.01)
*A61M 25/00* (2006.01)

(52) U.S. Cl.
CPC ........ *A61K 31/137* (2013.01); *A61K 31/4174* (2013.01); *A61M 25/0023* (2013.01); *A61M 25/0068* (2013.01)

(58) Field of Classification Search
None
See application file for complete search history.

(56) References Cited

U.S. PATENT DOCUMENTS

| | | | |
|---|---|---|---|
| 5,869,079 | A | 2/1999 | Wong et al. |
| 6,806,364 | B2 | 10/2004 | Su et al. |
| 8,313,763 | B2 | 11/2012 | Dadey et al. |

| | | | |
|---|---|---|---|
| 8,399,006 | B2 | 3/2013 | de Juan, Jr. et al. |
| 8,808,256 | B2 | 8/2014 | Beaton et al. |
| 8,808,727 | B2 | 8/2014 | de Juan, Jr. et al. |
| 9,417,238 | B2 | 8/2016 | Reich et al. |
| 10,656,152 | B2 | 5/2020 | de Juan, Jr. et al. |
| 10,835,416 | B2 | 11/2020 | de Juan et al. |
| 10,874,548 | B2 | 12/2020 | de Juan, Jr. et al. |
| 11,065,151 | B2 | 7/2021 | de Juan, Jr. et al. |
| 2006/0210604 | A1 | 9/2006 | Dadey et al. |
| 2009/0306454 | A1 | 12/2009 | Cockerham et al. |
| 2013/0110101 | A1* | 5/2013 | Van Valen .......... A61F 9/00718 606/33 |
| 2017/0281408 | A1 | 10/2017 | Arai et al. |
| 2018/0325806 | A1 | 11/2018 | Litvack et al. |
| 2020/0030142 | A1 | 1/2020 | Erickson et al. |
| 2020/0038240 | A1 | 2/2020 | de Juan, Jr. et al. |
| 2021/0025885 | A1 | 1/2021 | de Juan, Jr. et al. |

FOREIGN PATENT DOCUMENTS

| | | |
|---|---|---|
| DE | 1117588 | 11/1961 |
| WO | WO 2019/192109 A1 | 10/2019 |

OTHER PUBLICATIONS

Berge et al. "Pharmaceutical Salts", J. Pharm. Sci. 66:1-19, 1977.
Kim et al. "A Comparison of Vitamin A and Cyclosporine A 0.05% Eye Drops for Treatment of Dry Eye Syndrome", Am J Ophthalmol 147:206-13, 2009.

* cited by examiner

*Primary Examiner* — Bong-Sook Baek
(74) *Attorney, Agent, or Firm* — Knobbe, Martens, Olson & Bear, LLP

(57) ABSTRACT

Provided herein is a drug eluting device that can be implanted into the Muller's muscle of a subject to elute a sympathetic stimulant such as oxymetazoline, phenylephrine, norepinephrine, adrenaline, or a combination thereof. Also provided herein are methods to use the device and sympathetic stimulant to treat or prevent eyelid ptosis.

8 Claims, 3 Drawing Sheets

METHODS AND DEVICES FOR TREATMENT OF EYELID PTOSIS

INCORPORATION BY REFERENCE TO ANY PRIORITY APPLICATIONS

Any and all applications for which a foreign or domestic priority claim is made are identified in the Application Data Sheet as filed with the present application and are hereby incorporated by reference under 37 CFR 1.57.

BACKGROUND

Field

The present application generally relates to methods and devices for treatment of eyelid ptosis (i.e. droopy eyelid).

Description of the Related Art

A droopy eyelid can cover the center of the pupil, limiting a patient's vision. Senile aponeurotic dehiscence is a common cause of droopy eyelids.

In some cases, a droopy eyelid may be treated by surgical intervention. Surgical intervention may be through an external eyelid crease incision or an internal Muller's Muscle-Conjunctival Resection. Such surgical intervention may be costly and may not be appropriate for all patients with eyelid ptosis. Therefore, there is a need for an alternative, cheaper and less complicated treatment for eye ptosis.

Muller's muscle is a muscle in the upper eyelid. Conjunctival mullerectomy, wherein the upper eyelid is lifted, is based on the principle that the Muller's muscle, which is attached to the tarsal plate, is innervated by the sympathetic nervous system. The sympathetic nervous system, when activated, sends a "fight or flight" signal to the Muller's muscle lifting it an average of 2 mm. This nervous system pathway may be used to determine sensitivity of the Muller's muscle to sympathetic innervation as well as treatment of eyelid ptosis.

In some cases, pharmacological solutions, based upon the sympathetic nervous system pathway and its innervation of the Muller's muscle, may be used to activate the Muller's muscle to lift the upper eyelid for treatment of eyelid ptosis. However, pharmacological solutions merely added under the eyelid may often get washed out and may result in ineffective treatment of eyelid ptosis.

Neurotransmitters, such as norepinephrine or adrenaline, may also be used to treat eyelid ptosis. However, these and other neurotransmitters are often short-acting, presenting a challenge in using them for long-term eyelid ptosis correction.

Therefore, there is also a need for a delivery system that can efficiently deliver pharmacological solutions and/or neurotransmitters that activate the Muller's muscle for a longer timeframe to efficiently treat eyelid ptosis.

SUMMARY

The embodiments disclosed herein each have several aspects, of which no single one is solely responsible for the disclosure's desirable attributes. Without limiting the scope of this disclosure, the prominent features are briefly discussed herein. After considering this discussion, and particularly after reading the section entitled "Detailed Description," one will understand how the features of the embodiments described herein provide for efficient, cheaper, and less complicated eye ptosis treatment(s).

The following disclosure describes non-limiting examples of some embodiments. For instance, other embodiments of the disclosed method(s) and device(s) for treatment of eyelid ptosis may or may not include the features described herein. Moreover, disclosed advantages and benefits may apply only to certain embodiments and should not be used to limit the disclosure.

Various embodiments of the various aspects may be implemented.

Methods and Devices for treatment of eyelid ptosis are described herein. An eluting device may include at least one drug and/or at least one compound that may directly or indirectly activate the sympathetic nervous system, and consequently the Muller's muscle, potentially lifting an eyelid 2 mm, thereby correcting eyelid ptosis in patients. The eluting device may be implantable. The eluting device may include at least one drug and/or at least one compound that may facilitate long-term eyelid ptosis correction by activating post ganglionic Adrenergic receptors in an eyelid.

In one aspect, a drug eluting device for treatment of eyelid ptosis is disclosed. The drug eluting device may include, for example, a length between 3 mm and 4 cm and including a sympathetic stimulant, the device configured to elute at least 0.2 cc for at least one month.

In some embodiments, the stimulant includes oxymetazoline, phenylephrine, norepinephrine or adrenaline. In some embodiments, the stimulant may further include a biodegradable material. In some embodiments, the biodegradable material may be selected from the group consisting of PLGA, hyaluronic acid, hydroxyapatite, and chitosan. In some embodiments, the stimulant may further include an ophthalmologically acceptable carrier.

In another aspect, an injection device for injecting a drug eluting device into a Muller's muscle for the treatment of eyelid ptosis is disclosed. The injection device may include, for example, a catheter. In some embodiments, the catheter may include a length between 10 mm and 25 mm. In some embodiments, the catheter may include a size between 16 gauge and 28 gauge. In some embodiments, the catheter may include a bend.

In another aspect, an eyelid ptosis treatment kit is disclosed. The kit may include, for example, a drug eluting device and an injection device. In some embodiments, the kit may include both devices in a single sterilized packaging.

In some embodiments, the kit is a single dose kit. In some embodiments, the kit is a multi-dose kit.

In another aspect, a method for treating eyelid ptosis is disclosed. The method may include, for example, injecting a drug eluting device into a Muller's muscle. The method may include, for example, administering a sympathetic stimulant at a Muller's muscle, wherein the drug eluting device is configured to elute a sympathetic stimulant.

In some embodiments, the drug eluting device may include a biodegradable material. In some embodiments, the biodegradable material may include at least one of a gel, a synthetic copolymer, a nanoparticle, hyaluronic acid and PLGA, and/or a combination thereof.

In some embodiments, the drug eluting device may be further configured to elute oxymetazoline, phenylephrine, epinephrine, a parasympathetic blockade agent, and/or a combination thereof. In some embodiments, the administering may result in at least a 1 mm increase in the vertical separation of the upper and lower lids of the eye. In some embodiments, the administering may be administered once a month. In some embodiments, the administering may elute at least 0.1 cc of the oxymetazoline, phenylephrine, norepi-nephrine, adrenaline, and/or a combination thereof for at least one month. In some embodiments, the administering may result in at least a 10 percent increase in the vertical separation of the upper and lower lids of the eye. In some embodiments, the oxymetazoline, phenylephrine, epineph-rine, a parasympathetic blockade agent, and/or a combina-tion thereof may be formulated as a pharmaceutical com-position. In some embodiments, the pharmaceutical composition may further include an ophthalmologically acceptable carrier.

In some embodiments, the drug eluting device may include a length between 3 mm and 4 cm. In some embodi-ments, the injection device may include a catheter. In some embodiments, the catheter may include a length between 10 mm and 25 mm. In some embodiments, the catheter may include a size between 16 gauge and 28 gauge. In some embodiments, the catheter may include a bend.

BRIEF DESCRIPTION OF THE DRAWINGS

The features of the present disclosure will become more fully apparent from the following description and appended claims, taken in conjunction with the accompanying draw-ings. Understanding that these drawings depict only several embodiments in accordance with the disclosure and not to be considered limiting of its scope, the disclosure will be described with additional specificity and detail through use of the accompanying drawings. In the following detailed description, reference is made to the accompanying draw-ings, which form a part hereof. In the drawings, similar symbols typically identify similar components, unless con-text dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, may be arranged, substituted, combined, and designed in a wide variety of different configurations, all of which are explicitly contemplated and made part of this disclosure.

DETAILED DESCRIPTION

The following detailed description is directed to certain specific embodiments of methods and devices for treatment of eyelid ptosis. In this description, reference is made to the drawings wherein like parts or steps may be designated with like numerals throughout for clarity. Reference in this specification to "one embodiment," "an embodiment," or "in some embodiments" means that a particular feature, struc-ture, or characteristic described in connection with the embodiment is included in at least one embodiment of the disclosure. The appearances of the phrases "one embodi-ment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodi-ments but may not be requirements for other embodiments. The embodiments of the disclosure, examples of which are illustrated in the accompanying drawings, are set forth in detail below. Wherever possible, the same reference num-bers are used throughout the drawings to refer to the same or like parts.

Disclosed herein are methods and devices for treatment of eyelid ptosis, including an injection device and an injectable device. The injectable device may be a drug eluting device placed into the eyelid that may activate the Muller's muscle for long-term treatment of eyelid ptosis. The injectable device may be implanted into an eyelid in a minimally invasive way. The injectable device may, for example, be implanted into an eyelid with an injection device. The injectable device may release a material that may directly or indirectly activate the Muller's muscle and lift an eyelid. This activation may occur over an extended period of time, thereby limiting a need for invasive incisional surgery and/or anesthesia.

The disclosed injection device and injectable device may be used in patients who are poor surgical candidates, chil-dren, ill adults, and/or patients admitted in a hospital with multiple active medical issues.

Device

Figure 1A:
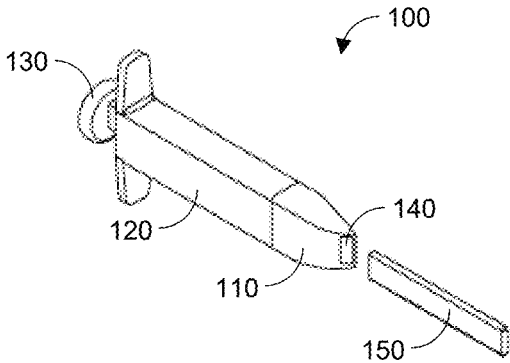
FIG. 1A illustrates a perspective view of an embodiment of an injection device and an embodiment of an injectable device.
Figure 1B:
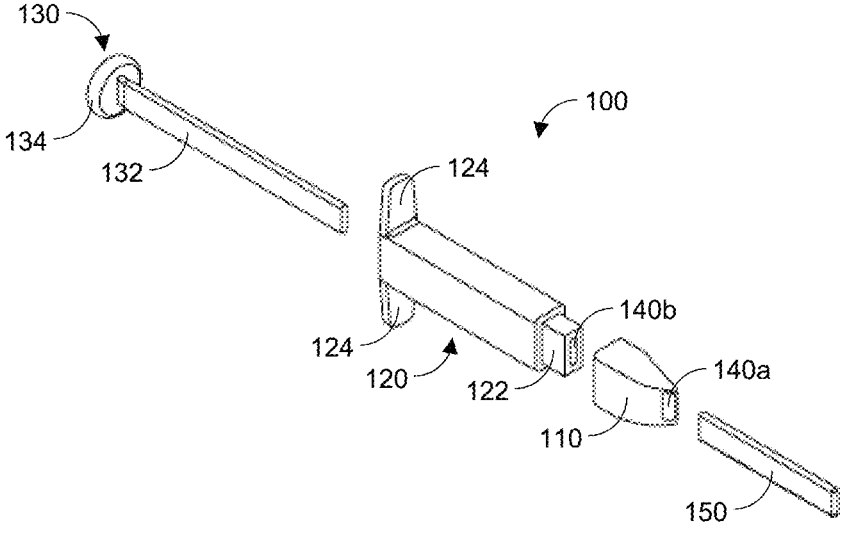
FIG. 1B illustrates an exploded perspective view of the embodiments of FIG. 1A.

FIG. 1A illustrates a perspective view of an embodiment of an injection device 100 and an embodiment of an inject-able device 150. FIG. 1B illustrates exploded perspective views thereof. In some embodiments, the injection device 100 and the injectable device 150 may be used to treat a droopy eyelid. In some embodiments, the injectable device 150 may be a drug eluting device.

In some embodiments, the injection device 100 may include a distal portion 110. In some embodiments, the injection device 100 may include a grip 120. In some embodiments, the injection device 100 may include a plunger 130. In some embodiments, the distal portion 110 may be configured with an internal cavity. The internal cavity may have different shapes and/or sizes, including, but not limited to, cylindrical, oval, square, rectangular, pyra-midal, triangular, and trapezoidal, or a combination thereof. In some embodiments, the internal cavity may define a lumen 140. The lumen 140 may have different shapes and/or sizes, including, but not limited to, square, rectangular, triangular, and trapezoidal, or a combination thereof. In some embodiments, the grip 120 may be configured with an internal cavity that may define the lumen 140. The internal cavity may have different shapes and/or sizes, including, but not limited to, cylindrical, oval, square, rectangular, pyra-midal, triangular, and trapezoidal, or a combination thereof. In some embodiments, the lumen 140 may be continuous through the distal portion 110 and grip 120. In some embodi-ments, the lumen 140 may be configured such that the injectable device 150 may pass through the lumen 140. In some embodiments, the distal portion 110 of the injection device 100 may be configured to allow access to an interior portion of an eye region (depicted in FIG. 3).

In some embodiments, the distal portion 110 may include a proximal port 112 (not shown). In some embodiments, the proximal port 112 may have different shapes and/or sizes, including, but not limited to, square, rectangular, circular, oval, and triangular, or a combination thereof.

In some embodiments, the grip 120 may include a distal end 122. The distal end 122 may have different shapes and/or sizes, including, but not limited to, square, rectangular, pyramidal, cylindrical, oval, and trapezoidal, or a combination thereof. In some embodiments, the distal end 122 of the grip 120 may be configured to mate with the proximal port 112 of the distal portion 110. Advantageously, such a configuration may allow a single embodiment of the grip 120 to be used with different embodiments of the distal portion 110. Such a configuration may also allow a single embodiment of the distal portion 110 to be used with different embodiments of the grip 120.

In some embodiments, the distal end 122 may include at least one connector 160 (not shown) to facilitate connection to another portion of the injection device 100. The connector 160 may include a clamp, threading, components for a snap-lock connection, components of another connector, or a combination thereof. In some embodiments, the proximal port 112 of the distal portion 110 may include at least one connector 170 (not shown) to facilitate connection to another portion of the injection device 100. The connector 170 may include a clamp, threading, components for a snap-lock connection and/or components of another connector, or a combination thereof.

In some embodiments, the distal portion 110 may include a first lumen portion 140*a*. In some embodiments, the grip 120 may include a second lumen portion 140*b*. In some embodiments, dimensions of the first lumen portion 140*a* may be approximately the same dimensions of the second lumen portion 140*b*, such that when the distal end 122 of the grip 120 is mated with the proximal port 112 of the distal portion 110, the lumen 140 may be continuous through at least a portion of the grip 120 and at least a portion of the distal portion 110.

In some embodiments, the plunger 130 may include a rod 132. The rod 132 may have different shapes and/or sizes, including, but not limited to, cylindrical, oval, rectangular, square, conical, and trapezoidal, or a combination thereof. In some embodiments, the plunger 130 may include a cap 134. The cap 134 may have different shapes and/or sizes, including, but not limited to, square, rectangular, circular, and oval, or a combination thereof. In some embodiments, the rod 132 may be dimensioned to be inserted into a proximal port 142 (not shown) of the grip 120. In some embodiments, the rod 132 may be inserted into the proximal port 142 of the grip by a user pressing the cap 134. In some embodiments, the rod 132 may be inserted at least partially into the lumen 140 by a user pressing the cap 134. In some embodiments, such a motion may be facilitated by including at least one wing 124 around the proximal port 142 of the grip 120. In some embodiments, the at least one wing 124 may be configured such that a user may hold the grip 120 by the at least one wing 124 while pressing the cap 134 to insert the rod 132 into the lumen 140. In some embodiments, a motion of the plunger 130 into the lumen 140 may be used to urge the injectable device 150 through the lumen 140.

In some embodiments, the lumen 140 may have an opening configured to receive at least one material to be inserted into a body, including, but not limited to, catheter and/or the injectable device 150. In some embodiments, the lumen 140 may be configured to be a pathway for insertion of the at least one material into an interior portion of an eye or an eyelid.

In some embodiments, the distal portion 110 of the injection device 100 may further include a distal end 125 (not shown). In some embodiments, the distal end 125 may be configured to mate with at least one other device. The at least one other device may include, not limited to, an elongated tube, needle, and/or catheter, or a combination thereof. In some embodiments, dimensions of the other device may be approximately the same dimensions as the lumen 140. In some embodiments, the at least one other device may be positioned on the distal portion 110 such that a lumen of the at least one other device aligns with the lumen 140. In some embodiments, the lumen of the at least one other device may be an extension of the lumen 140. In some embodiments, the at least one other device may include a flexible body, which may facilitate insertion of the injectable device 150 into an eye or eyelid at an angle different from the angle of entry into the body. In some embodiments, the flexible body may include a bend. In some embodiments, the at least one other device may be a catheter. In some embodiments, the catheter may have different lengths. In some embodiments, a length of the catheter may include a length in a range of 10 mm and 25 mm. In some embodiments, the catheter may include different sizes. In some embodiments, the catheter may include a size in a range of 16 gauge and 28 gauge. In some embodiments, the catheter may include a bevel at a distal tip thereof.

In some embodiments, the proximal port 112 of the distal portion 110 may receive the distal end 122 of the grip 120 to form a secure connection. In some embodiments, the plunger 130 may advance the injectable device 150 through the lumen 140. In some embodiments, the plunger 130 may advance the injectable device 150 beyond the lumen 140 and insert the injectable device 150 into, for example, a portion of an eye or eyelid of a subject. In some embodiments, at least one additional component may be included, for example, a wire which may be used to advance the injectable device 150 into the body. In some embodiments, the wire may extend and/or fit through the other device, including a catheter.

In some embodiments, the injectable device 150 may be at least one drug-eluting device. In some embodiments, the at least one drug may include drugs that activate the Muller's muscle. In some embodiments, the drug eluting device may be placed into the eyelid. In some embodiments, the drug eluting device may be configured to deliver the at least one drug into the eyelid to activate the Muller's muscle for a long-term result. In some embodiments, the injectable device 150 may be implanted into the eyelid in a minimally invasive way. In some embodiments, the injectable device 150 may be implanted into the eyelid by the injection device 100. In some embodiments, the injectable device 150 may release at least one sympathetic stimulant that may activate the Muller's muscle. The at least one sympathetic stimulant may include, not limited to, norepinephrine and/or adrenaline. In some embodiments, a long-term activation may occur over an extended period, limiting the need for invasive incisional surgery and/or anesthesia. In some embodiments, the injectable device 150 may be configured to elute 0.2-3.0 cc of the at least one sympathetic stimulant over an extended period of time. The period of time may include, days, months, or years. In some embodiments, the injectable device 150 may be configured to continuously elute a sufficient dosage of the at least one sympathetic stimulant for a period of 1 month to 5 years.

Figure 2A:
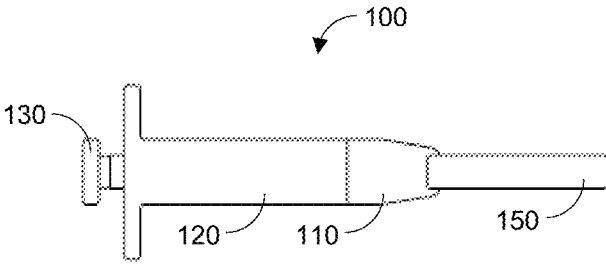
FIG. 2A illustrates a side view of the injection device embodiment of FIG. 1A coupled to the injectable device embodiment of FIG. 1A.
Figure 2B:
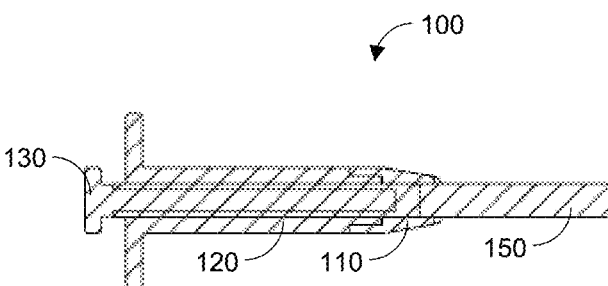
FIG. 2B illustrates a cross-sectional side view of the embodiments of FIG. 2A.

FIG. 2A illustrates a side view of an example embodiment of the injection device 100 coupled to an example embodiment of the injectable device 150. FIG. 2B illustrates a cross-sectional side view of an example embodiment of the injection device 100 coupled to an example embodiment of the injectable device 150. In some embodiments, the injectable device 150 may be generally elongated. In some embodiments, a length of the injectable device 150 may include a length in a range of 3 mm and 4 cm. In some embodiments, the length of the injectable device 150 may generally match a length of the tarsal plate.

Figure 3:
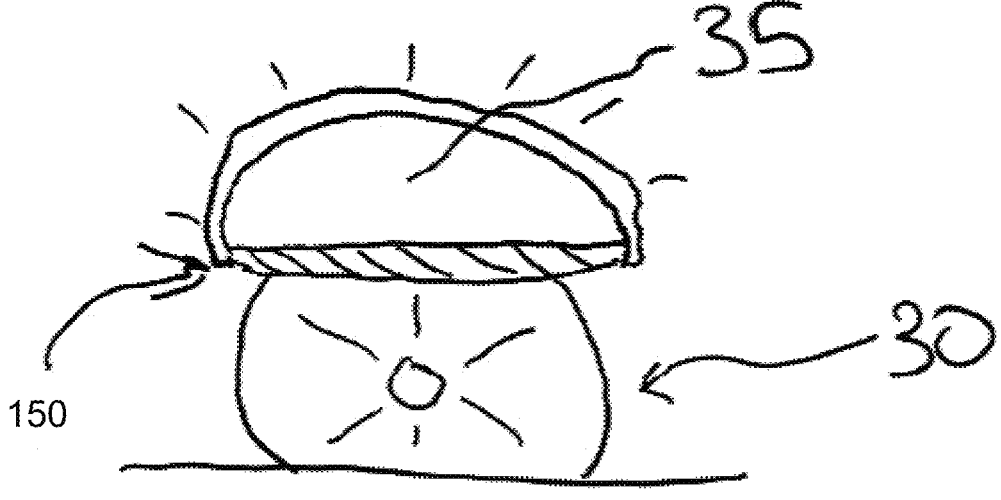
FIG. 3 illustrates a frontal view of an eye and an everted eyelid showing an example insertion site of an injectable device.
Figure 4:
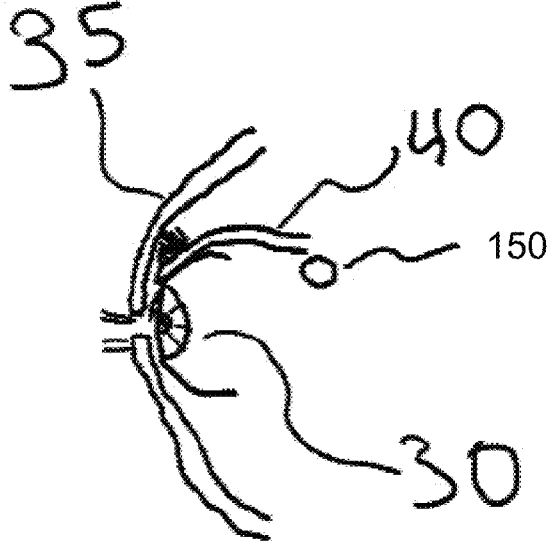
FIG. 4 illustrates a cross-sectional side view of an eye and an eyelid showing an example insertion site of an injectable device.

FIG. 3 illustrates a frontal view of an eye and an everted eyelid showing an example insertion site of the injectable device 150. FIG. 4 illustrates a cross-sectional side view of the example insertion site. In some embodiments, the injectable device 150 may be implanted near an eye 30 and an eyelid 35. In some embodiments, the injectable device 150 may be implanted near the eye 30 and near the eyelid 35, and near the Muller's muscle 40. In some embodiments, the injectable device 150 may be implanted in the eyelid to avoid an eluted drug from affecting other muscles or tissues.

In some embodiments, the injectable device 150 may include at least one biodegradable material. The at least one biodegradable material may include, for example, gels, synthetic polymers, nanoparticles, PEG-PCL, hyaluronic acid and PLGA, or a combination thereof. In some embodiments, the gels may include hyaluronic acid and sodium hyaluronate. In some embodiments, the synthetic copolymers or nanoparticles may include for example, poly lactic-co-glycolic acid (PLGA), poly(ethylene glycol)-poly(ε-caprolactone) (PEG-PCL), or another poly(ethylene glycol)-based (PEG) gel. In some embodiments, the hyaluronic acid and PLGA may include, not limited to, Restylane® and/or dexamethasone intravitreal implant (Ozurdex®).

In some embodiments, the injectable device 150 may provide at least one therapeutic agent for ptosis correction. In some embodiments, the at least one therapeutic agent may be a sympathomimetic medication. In some embodiments, the sympathomimetic medication may include, not limited to, oxymetazoline, phenylephrine, epinephrine, and a parasympathetic blockade agent, or a combination thereof. Oxymetazoline is 3-(4,5-dihydro-1H-imidazol-2-ylmethyl)-2,4-dimethyl-6-tert-butyl-phenol, CAS number 1491-59-4. Oxymetazoline was developed from xylometazoline at E. Merck Darmstadt by Fruhstorfer in 1961 (German Patent 1,117,588).

In some embodiments, the sympathomimetic medication may include an alpha-adrenergic agonist. The alpha-adrenergic agonist may include, not limited to, midodrine, brimonidine, epinephrine, apraclonidine, phenylephrine, norepinephrine, phenylpropanolamine, clonidine, metaraminol, guanabenz, dexmedetomidine, tizanidine, methoxamine, oxymetazoline, methyldopa, guanfacine, mephentermine, oxymetazoline, methyldopa, guanfacine, mephentermine, lofexidine, xylometazoline, naphazoline, adrafinil, etilefrine, cirazoline, synephrine, racepinephrine, amitraz, medetomidine, xylazine, romifidine, detomidine, rilmenidine, octopamine, norfenefrine, pseudoephedrine, ephedrine, cipivefrin, droxidopa, pergolide, bromocriptine, ephedra sinica root, metamfetamine, moxonidine, DL-methylephedrine, phendimetrazine, ergometrine, isometheptene, tetryzoline, etomidate, bethanidine, dobutamine, benzphetamine, 4-methoxyamphetamine, 4-bromo-2, 5-dimethoxyphenethylamine, amidephrine, propylhexedrine.

In some embodiments, the sympathomimetic medication may include a beta-adrenergic agonist. The beta-adrenergic agonist may include, not limited to, dobutamine, dobutamine, isoctharine, orciprenaline, ritodrine, terbutaline, bitolterol, salmeterol, formoterol, salbutamol, arbutamine, arformoterol, fenoterol, pirbuterol, procaterol, clenbuterol, nebivolol, amibegron, nylidrin, solabegron, mirabegron, isoxsuprine, hexoprenaline, etilefrine, befunolol, olodaterol, racepinephrine, ractopamine, ritobegron, tulobuterol, dopexamine, higenamine, reproterol, oxyfedrine, rimiterol, methoxyphenamine, tretoquinol, prenalterol, xamoterol, ephedrine, abediterol, indacaterol, levosalbutamol, norepinephrine, bambuterol, droxidopa, dipivefrin, ephedra sinica root, phenylpropanolamine, vilanterol, celiprolol, doxofylline, protokylol, etafedrine, PF-00610355, pseudoephedrine, batefenterol, vibegron.

Pharmaceutical Composition(s)

In some embodiments, the at least one therapeutic agent may be formulated as at least one pharmaceutical composition. In some embodiments, the at least one pharmaceutical composition may be formulated with at least one ophthalmologically acceptable carrier. In some embodiments, the at least one pharmaceutical composition may include the at least one therapeutic agent in a concentration range that may include, not limited to, 0.05, 0.1, 0.2, 0.3, 0.4, 0.5, 0.6, 0.7, 0.8, 0.9, 1.0, 2.0, 3.0, 4.0, 5.0 weight percent, or ranges including and/or spanning the aforementioned values. An "ophthalmologically acceptable carrier" may be any pharmaceutically acceptable carrier suitable for topical administration to an eye.

In some embodiments, the at least one therapeutic agent may be a pharmaceutically acceptable salt of oxymetazoline. The term "pharmaceutically acceptable salts" is art-recognized, and refers to relatively non-toxic, inorganic and organic acid addition salts of compositions of the present disclosure or any components thereof, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include but are not limited to the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and tri-alkylamines, such as methylamine, dimethylamine, and triethylamine; mono-, di- or tri-hydroxyalkylamines such as mono-, di-, and tri-ethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)amino-ethane; and the like. Sec, for example, Berge et al. (1977) J. Pharm. Sci. 66:1-19. In some embodiments, the pharmaceutically acceptable salt of oxymetazoline may be oxymetazoline hydrochloride.

In some embodiments, where the oxymetazoline may be provided as a pharmaceutically acceptable salt, the weight percent oxymetazoline may be based on the oxymetazoline component alone. In some embodiments, where the oxymetazoline may be provided as a pharmaceutically acceptable salt, the weight percent oxymetazoline may be based on the oxymetazoline salt.

In some embodiments, the at least one pharmaceutical composition may include at least one additional active agent. In some embodiments, the at least one pharmaceutical composition may include at least one antioxidant. An antioxidant is a molecule capable of inhibiting the oxidation of other molecules. Oxidation is a chemical reaction that transfers electrons from a substance to an oxidizing agent. Oxidation reactions can produce free radicals. In turn, these radicals may start chain reactions that damage cells. Antioxidants terminate these chain reactions by removing free radical intermediates and inhibit other oxidation reactions. They do this by being oxidized themselves, so antioxidants are often reducing agents such as thiols, ascorbic acid or polyphenols. Antioxidants are classified into two broad divisions, depending on whether they are soluble in water (hydrophilic) or in lipids (hydrophobic). In general, water-soluble antioxidants react with oxidants in the cell cytosol and the blood plasma, while lipid-soluble antioxidants protect cell membranes from lipid peroxidation. Water-soluble antioxidants include, without limitation, ascorbic acid (vitamin C), glutathione, lipoic acid, and uric acid. Lipid-soluble antioxidants include, without limitation, carotenes (e.g., alpha-carotene, beta-carotene), alpha-tocopherol (vitamin E), and ubiquinol (coenzyme Q). In some embodiments, the antioxidant may be N-acetylcarnosine. In some embodiments, the antioxidant may be sodium metabisulfite.

In some embodiments, the at least one pharmaceutical composition may include vitamin A (retinol). When converted to the retinal (retinaldehyde) form, vitamin A is essential for vision, and when converted to retinoic acid, is essential for skin health and bone growth. These chemical compounds are collectively known as retinoids and possess the structural motif of all-trans retinol as a common feature in their structure. Topical vitamin A, for example, in the form of eye drops containing retinyl palmitate 0.05 percent, has been reported to be effective treatment for dry eye (also known as keratoconjunctivitis sicca, xerophthalmia, and dry eye syndrome). Kim et al. (2009) Am J Ophthalmol 147: 206-13. Vitamin A has also been formulated at a strength of 50,000 units/mL for ophthalmic use.

In some embodiments, the at least one pharmaceutical composition may include at least one astringent. Astringents include, but are not limited to, witch hazel, zinc sulfate, silver sulfate, plant tannins, oak bark extract, bird cherry extract, and natural flavinoids. In some embodiments, the astringent may be witch hazel, which is an astringent produced from the leaves and bark of the North American Witch Hazel shrub (*Hamamelis virginiana*), which grows naturally from Nova Scotia west to Ontario, Canada, and south to Florida and Texas in the United States. Witch hazel is readily available from commercial suppliers, including Dickinson's and Henry Thayer.

In some embodiments, the at least one pharmaceutical composition may include at least one inert or non-active agent. In some embodiments, the at least one pharmaceutical composition may include at least one ocular lubricant. Ocular lubricants include, not limited to, solutions, gels, or ointments formulated to moisturize the eyes, including artificial tears, widely available from any of a variety of commercial suppliers. In some embodiments, the at least one ocular lubricant may include an aqueous solution of a polyalcohol (polyol) such as polyvinyl alcohol, borate, and/ or a buffer. In some embodiments, the at least one ocular lubricant may include white petrolatum and/or mineral oil.

In some embodiments, the at least one pharmaceutical composition may include at least one blue dye, for example, methylene blue. The at least one blue dye may confer a lightening or whitening effect on an eye sclera, making "tired eyes" appear less tired.

In some embodiments, the at least one pharmaceutical composition may include at least one active ingredient formulated in an aqueous solution. In some embodiments, the at least one pharmaceutical composition may be formulated for topical administration including, but not limited to as, a solution, suspension, oil, viscous or semi-viscous gel, emulsion, liposome, lotion, ointment, cream, gel, salve, powder, and/or sustained or slow release, or other types of solid or semi-solid compositions, including formulations described in U.S. Pat. No. 6,806,364.

In some embodiments, the at least one pharmaceutical composition may include at least one tear substitute. A variety of tear substitutes are known in the art, including, but not limited to: polyols such as, glycerol, glycerin, polyethylene glycol 300, polyethylene glycol 400, polysorbate 80, propylene glycol, and ethylene glycol, polyvinyl alcohol, povidone, and polyvinylpyrrolidone; cellulose derivatives such hydroxypropyl methylcellulose (also known as hypromellose), carboxy methylcellulose sodium, hydroxypropyl cellulose, hydroxyethyl cellulose, and methylcellulose; dextrans such as dextran 70; water soluble proteins such as gelatin; carbomers such as carbomer 934P, carbomer 941, carbomer 940 and carbomer 974P; and gums such as HP-guar. Many such tear substitutes are commercially available, which include, but are not limited to cellulose esters such as Bion Tears®, Celluvisc®, Genteal®, OccuCoat®, Refresh® Teargen II®, Tears Naturale®, Tears Naturale 118®, Tears Naturale Free®, and TheraTears®; and polyvinyl alcohols such as Akwa Tears®, HypoTears®, Moisture Eyes®, Murine Lubricating®, and Visine Tears®. In other embodiments, the tear substitute is that which is described in U.S. Pat. No. 6,806,364, which is expressly incorporated by reference herein in its entirety. The formulation described in U.S. Pat. No. 6,806,364 contains 0.2 to 2.5 (e.g., 0.5 to 0.8) percent by weight of hydroxypropyl methylcellulose, 0.045 to 0.065 (e.g., 0.05 to 0.06) percent by weight a calcium salt, and 0.14 to 1.4 (e.g., 0.3 to 1.2) percent by weight a phosphate salt. The formulation described in U.S. Pat. No. 6,806,364 has a viscosity of 20 to 150 (e.g., 50 to 90) centipoise and is buffered to a pH 5.5 to 8.5 (e.g., 6 to 8) with a phosphate salt or other suitable salts. It may further contain one or more of the following ingredients: 0.5 to 1.0 percent by weight glycerol, 0.5 to 1.0 percent by weight propyleneglycerol, 0.005 to 0.05 percent by weight glycine, 0.006 to 0.08 percent by weight sodium borate, 0.025 to 0.10 percent by weight magnesium chloride, and 0.001 to 0.01 percent by weight zinc chloride.

The at least one tear substitute may include at least one paraffin, for example, commercially available Lacri-Lube® ointments. In some embodiments, the at least one pharmaceutical composition may include at least one other commercially available ointment used as a tear substitute including, but not limited to, Lubrifresh PM®, Moisture Eyes PM®, and Refresh PM®.

In some embodiments, the at least one pharmaceutical composition may not include a preservative. Such formulations may be useful for patients who wear contact lenses, or those who use several topical ophthalmic drops and/or those with an already compromised ocular surface (e.g. dry eye) wherein limiting exposure to a preservative may be desirable.

In some embodiments, the at least one pharmaceutical composition formulated as a topical formulation may include at least one solubilizer, in particular if the active or inactive ingredients tend to form a suspension or an emulsion. The at least one solubilizer may be selected from a group consisting of tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin, or panosyl-cyclodextrin), polysorbate 20, polysorbate 80, or mixtures of those compounds. In some embodiments, the at least one solubilizer may be a reaction product of castor oil and ethylene oxide, such as, for example, the commercial products Cremophor EL®, or Cremophor RH40®. Reaction products of castor oil and ethylene oxide have proved to be particularly good solubilizers that are tolerated extremely well by the eye. In some embodiments, the at least one solubilizer may be selected from tyloxapol and from a cyclodextrin. In some embodiments, the concentration used may depend on concentration of the active ingredient. In some embodiments, the amount added of the at least one solubilizer may be sufficient to solubilize the active ingredient. In some embodiments, a concentration of the at least one solubilizer may be from 0.1 to 5000 times a concentration of the active ingredient.

In some embodiments, the at least one pharmaceutical composition formulated as a topical formulation may include at least one non-toxic excipient. The at least one non-toxic excipient may be, but is not limited to, at least one emulsifier, and/or at least one wetting agent or filler, including, for example, polyethylene glycols designated 200, 300, 400 and 600, or Carbowax designated 1000, 1500, 4000, 6000 and 10000. In some embodiments, the amount and type of excipient added may be in accordance with specific requirements and may be in a range from approximately 0.0001 to approximately 90% by weight.

In some embodiments, at least one other compound may be added to increase a viscosity of the carrier. Examples of viscosity enhancing agents include, but are not limited to, polysaccharides, such as hyaluronic acid and its salts, chondroitin sulfate and its salts, dextrans, various polymers of the cellulose family; vinyl polymers; and acrylic acid polymers.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In some embodiments, a pharmaceutically acceptable carrier may be non-pyrogenic. Some examples of materials which may serve as pharmaceutically acceptable carriers include, but are not limited to, pyrogen-free water; aqueous solutions, suspensions, and ointments; isotonic saline; Ringer's solution; phosphate buffer solutions; borate solutions; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; ethyl alcohol; and other non-toxic compatible substances employed in pharmaceutical formulations.

Kits

In some embodiments, the injectable device 150 may be included in a single kit. In some embodiments, for example, the injectable device 150 may be included with the injection device 100 in a single sterilized packaging (not shown). In some embodiments, the injectable device 150 may be included in a separate sterilized packaging. In some embodiments, the injection device 100 may be included in a separate sterilized packaging.

In some embodiments, the at least one pharmaceutical composition may be packaged as a single-dose product. In some embodiments, the at least one pharmaceutical composition may be packaged as a multi-dose product. In some embodiments, the single-dose product may be sterile prior to opening of the package. In some embodiments, an entirety of the at least one pharmaceutical composition in the single-dose product package may be intended to be utilized in a single application to one or both eyes of a patient. In some embodiments, the at least one pharmaceutical composition may include at least one antimicrobial preservative to maintain sterility of the composition.

In some embodiments, a multi-dose product container may be configured to be opened many times. In some embodiments, the multi-dose product may be sterile. In some embodiments, the multi-dose product may be sterile only prior to opening of the package. In some embodiments, the multi-dose product may include at least one antimicrobial preservative sufficient to ensure that the at least one pharmaceutical composition may not become contaminated by microbes as a result of repeated opening and/or handling of the multi-dose product container. A level of antimicrobial activity required for this purpose is well known to those skilled in the art, and is specified in official publications, such as the United States Pharmacopoeia ("USP"), other publications by the Food and Drug Administration, and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing".)

In some embodiments, a use of a single-dose packaging arrangement may eliminate the need for an antimicrobial preservative in the at least one pharmaceutical composition. This may offer a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single-dose packaging arrangements currently available, such as small volume plastic vials prepared by means of a process known as "form, fill and seal", have several disadvantages for manufacturers and consumers. The principal disadvantages of the single-dose packaging systems are the much larger quantities of packaging materials required, which is both wasteful and costly, and the inconvenience for the consumer. Also, there is a risk that consumers will not discard the single-dose containers following application of one or two drops to the eyes, as they are instructed to do, but instead will save the opened container and any composition remaining therein for later use. This improper use of single-dose products creates a risk of microbial contamination of the single-dose product and an associated risk of ocular infection if a contaminated composition is applied to the eyes.

Methods of Use

In one aspect, a method for treating ptosis in a subject may include administering an effective amount of a therapeutic agent with an injectable device 150. In some embodiments, the method includes administering an effective amount of the therapeutic agent to an exterior surface of an eye of the subject in need. As used herein, "treating" means reducing, even if only temporarily, a severity of a condition or disease in a subject having such condition or disease. In some embodiments, the reducing is eliminating, even if only temporarily. In some embodiments, for example, ptosis in a subject is considered to be treated in accordance with the methods described herein if the ptosis is reduced or eliminated, even if only temporarily. Also as used herein, a "subject in need" is a subject having a condition in need of treatment. For example, in the context of this aspect of the disclosure, a subject in need of such treatment in a subject that has ptosis of at least one eyelid.

A subject has ptosis when at least the left or the right upper eyelid is subjectively or objectively ptotic compared to historical control and/or the other eye. In some embodiments, both the left and the right upper eyelid are ptotic, although not necessarily to the same degree.

In some embodiments, a subject is said to have ptosis when at least the left or the right upper eyelid is ptotic by at least one millimeter (mm) compared to historical control and/or the other eye. Such measurement involves measuring the widest separation of the upper and lower lids in the sagittal plane, typically but not necessarily across the center of the pupil, with the subject at rest, i.e., without any conscious effort on the part of the subject to widen the lids. In some embodiments, the measurement is made on the eye or eyes of a living subject. In some embodiments, the measurement is made or based on a photographic image of the subject's eye or eyes. In some embodiments, the administering of the therapeutic agent results in at least 1 mm increase in the vertical separation of the upper and lower lids of the eye. In some embodiments, the administering of the therapeutic agent results in at least 2 mm, at least 3 mm, at least 4 mm, at least 5 mm, at least 6 mm, at least 7, mm, at least 8 mm, at least 9 mm, at least 10 mm, or any ranges including and/or spanning the aforementioned values increase in the vertical separation of the upper and lower lids of the eye. In some embodiments, the administering of the therapeutic agent results in at least a 10 percent increase in the vertical separation of the upper and lower lids of the eye. In some embodiments, the administering of the therapeutic agent results in at least a 15 percent increase, at least a 20 percent increase, at least a 25 percent increase, at least a 30 percent increase, at least a 35 percent increase, at least a 40 percent increase, at least a 45 percent increase, at least a 50 percent increase, or any ranges including and/or spanning the aforementioned values in the vertical separation of the upper and lower lids of the eye.

In some embodiments, the effective amount of a therapeutic agent is administered to the eye or eyes intended for treatment. As used herein, an "effective amount" is an amount that is sufficient to achieve a desired biological result. For example, an effective amount of phenylephrine is an amount of phenylephrine that is sufficient to treat ptosis in a subject having ptosis. The effective amount may vary depending on factors including the disease or condition being treated and/or a severity of the disease or condition being treated. One of skill in the art may empirically determine an effective amount of a particular agent without necessitating undue experimentation. In some embodiments, the therapeutic agent includes an alpha-adrenergic agonist, a beta-adrenergic agonist, oxymetazoline, phenylephrine, epinephrine, a parasympathetic blockage agent, or a combination thereof. In some embodiments, the therapeutic agent may be formulated as a pharmaceutical composition including at least one active agent in an ophthalmologically acceptable carrier. The pharmaceutical composition may be formulated as a weight percent of the active agent. In some embodiments, for example, the oxymetazoline may be formulated as a pharmaceutical composition including at least 0.05 weight percent oxymetazoline in an ophthalmologically acceptable carrier. In some embodiments, the therapeutic agent includes at least two active agents. In some embodiments, for example, the therapeutic agent includes oxymetazoline and phenylephrine.

In some embodiments, a therapeutic agent to be administered is administered with the injectable device 150. In some embodiments, the injectable device 150 is a drug eluting device. In some embodiments, the drug eluting injectable device 150 has a length between about 3 mm and about 4 cm. In some embodiments, the drug eluting injectable device 150 has a length between about 0.5 cm and about 6 cm, about 0.5 cm and about 5 cm, about 0.5 cm and about 4 cm, about 0.5 cm and about 3 cm, about 0.5 cm and about 2 cm, about 0.5 cm and about 1 cm, about 1 cm and about 5 cm, about 1 cm and about 4 cm, about 1 cm and about 3 cm, about 1 cm and about 2 cm, or ranges including and/or spanning the aforementioned values.

In some embodiments, the drug eluting injectable device 150 is configured to elute at least 0.1 cc, at least 0.15 cc, at least 0.2 cc, at least 0.25 cc, at least 0.3 cc, at least 0.35 cc, at least 0.4 cc, at least 0.45 cc, at least 0.5 cc, or ranges including and/or spanning the aforementioned values, of the therapeutic agent for at least one month. In some embodiments, the drug eluting injectable device 150 is configured to elute at least 0.2 cc of the therapeutic agent for at least one month. In some embodiments, the therapeutic agent is administered once a month every month for at least three months.

In some embodiments, the administering may be performed by the subject. In some embodiments the administering may be performed by an individual other than the subject, e.g., by a health care provider, a parent, or a spouse.

Certain subjects may be excluded from the methods of the disclosure. In some embodiments, the subject does not have an allergic ocular condition calling for treatment of the eye with a therapeutic agent. In some embodiments, the subject does not have eyelid swelling. In some embodiments, the subject has not undergone refractive eye surgery. In some embodiments, the subject does not have an allergic ocular condition calling for treatment of the eye with oxymetazoline. In some embodiments, the subject does not have eyelid swelling and the subject has not undergone refractive eye surgery. In some embodiments, the subject does not have an allergic ocular condition calling for treatment of the eye with a therapeutic agent, does not have eyelid swelling, and has not undergone refractive eye surgery. Alternatively or in addition, in certain embodiments the subject does not have acute allergic conjunctivitis or non-infectious conjunctivitis.

The dosage of any compound of the present disclosure will vary depending on the symptoms, age, and other physical characteristics of the patient, the nature and severity of the disorder to be treated or prevented, the degree of comfort desired, the route of administration, and the form of the medicament. Any of the subject formulations may be administered in a single dose or in divided doses. Dosages for the formulations of the present disclosure may be readily determined by techniques known to those of skill in the art or as taught herein.

An effective dose or amount, and any possible effect on timing of administration of the formulation, may need to be identified for any formulation of the present disclosure. This may be accomplished by routine experiment as described herein. The effectiveness of any formulation and method of treatment or prevention may be assessed by administering the formulation and assessing the effect of the administration by measuring one or more indices associated with the efficacy of the agent and with the degree of comfort to the patient, as described herein, and comparing the post-treatment values of these indices to the values of the same indices prior to treatment or by comparing the post-treatment values of these indices to the values of the same indices using a different formulation.

A precise time of administration and amount of any formulation that may yield the most effective treatment in a given patient may depend upon the activity, pharmacokinetics, and bioavailability of a particular compound, physiological condition of the patient (including age, sex, disease type and stage, general physical condition, responsiveness to a given dosage and type of medication), and the like. The guidelines presented herein may be used to optimize the treatment, e.g., determining an optimum time and/or amount of administration, which will require no more than routine experimentation consisting of monitoring the subject and adjusting the dosage and/or timing.

A combined use of several agents formulated into the compositions of the present disclosure may reduce the required dosage for any individual component because the onset and duration of effect of the different components may be complimentary or even synergistic. In such combined therapy, the different agents may be delivered together or separately, and simultaneously or at different times within the day.

EXAMPLES

Example 1

The mammalian metabolic system uses neuroendocrine pathways to stimulate the rest and digest, fight or flight pathways in the body. This allows the body to rest, digest and reproduce with the parasympathetic system and fight, run and increase blood flow to the large organs like the heart and muscles for defense and escape in the sympathetic system. The sympathetic nervous system courses through the entire body, delivering needed stimulation during times of stress.

The human eyelid along with the human pupil are innervated by both systems. Norepinephrine or (noradrenaline) activates a small muscle in the upper eyelid (Müllers muscle) and lower eyelid (inferior tarsal muscle), by activating the postsynaptic neuromuscular (NM) receptors. Müllers muscle is easily found by flipping the upper eyelid and is below the palpebral conjunctiva, it attaches to the superior edge of the tarsal plate. Phenylephrine (PE), a sympathomimetic drug already FDA approved for the eye, has been shown to lift the eyelid by activating post synaptic neuromuscular junction and activating muscle contraction as it does in cardiac muscle. This medication and technique are well-established techniques used in the medical office for dilating the human pupil and determination of healthy sympathomimetic response to PE. Off label use of PE allows the eyelid specialist to determine if surgical advancement of the Müllers muscle will resolve active upper eyelid ptosis. The sympathomimetic activity can also retract or lower the lower eyelid for cosmetic or functional reasons.

Tunable, sustainable, biodegradable polymers may be the material used for delivery of the drug for the treatment of ptosis. PLGA and Hyaluronic acid, hydroxyapatite and Chitosan for example are established polymers for use in the treatment of medical conditions. These polymers have been studied for over 30-40 years and have already been approved for other injectable medical devices. These molecules are either naturally occurring or engineered. They are well tolerated and are enzymatically or non-enzymatically eliminated in vivo. The end products of metabolism are eliminated via normal metabolic pathways. These polymers and molecules among others and in combination may be used for the purpose of delivering medications that may treat eyelid ptosis, undesirable cosmetic eyelid positions as well as for the delivery of new therapeutic agents to the orbital, eyelid and periocular tissues, for example, treatment of infections and inflammations, such as chalazion styes and rosacea and idiopathic orbital inflammation.

Various modifications to the embodiments described in this disclosure will be readily apparent to those skilled in the art, and the generic principles defined herein may be applied to other embodiments without departing from the spirit or scope of this disclosure. Thus, the disclosure is not intended to be limited to the embodiments discussed herein but is to be accorded the widest scope consistent with the claims, the principles and the novel features disclosed herein. The word "example" is used exclusively herein to mean "serving as an example, instance, or illustration." Any embodiment described herein as "example" is not necessarily to be construed as preferred or advantageous over other embodiments, unless otherwise stated.

Certain features that are described in this specification in the context of separate embodiments also may be embodied in combination in a single embodiment. Conversely, various features that are described in the context of a single embodiment also may be embodied in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the order shown or in sequential order, or that all illustrated operations be performed, to achieve desirable results. Additionally, other embodiments are within the scope of the following claims. In some cases, the actions recited in the claims may be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

For example, the phrase "A or B" will be understood to include the possibilities of "A" or "B" or "A and B."

What is claimed is:

1. A drug eluting device for treatment of eyelid ptosis, the drug eluting device having an elongate shape and a length between 3 mm and 4 cm, the drug eluting device comprising a biodegradable polymer and a sympathetic stimulant composition comprising between 0.05 to 5.0 weight percentage of oxymetazoline, wherein the drug eluting device is configured to elute at least 0.2 cc of the sympathetic stimulant composition for at least one month, and wherein the drug eluting device is further configured to be injected into a Muller's muscle of a patient using an injection device configured to allow access to an interior portion of an eye region.

2. The drug eluting device of claim 1, wherein the biodegradable polymer is selected from the group consisting of PLGA, PEG-PCL, hyaluronic acid, hydroxyapatite, and chitosan.

3. The drug eluting device of claim 1, wherein the sympathetic stimulant composition further comprises an ophthalmologically acceptable carrier.

4. The drug eluting device of claim 1, wherein the sympathetic stimulant composition further comprises phenylephrine, epinephrine, a parasympathetic blockade agent, or a combination thereof, and wherein the sympathetic stimulant composition is formulated as a pharmaceutical composition comprising an ophthalmologically acceptable carrier.

5. The drug eluting device of claim 1, wherein the length of the drug eluting device corresponds with the length of a tarsal plate of a ptotic eye of the patient.

6. The drug eluting device of claim 1, wherein the biodegradable polymer comprises PEG-PCL.

7. The drug eluting device of claim 1, wherein the biodegradable polymer comprises hyaluronic acid.

8. The drug eluting device of claim 1, wherein the biodegradable polymer comprises chitosan.

* * * * *